United States Patent [19]
Schoepe

[11] Patent Number: 5,636,019
[45] Date of Patent: Jun. 3, 1997

[54] AIR-IN-WATER INDICATOR

[75] Inventor: Adolf Schoepe, Anahiem, Calif.

[73] Assignee: Fluidmaster, Inc., Anaheim, Calif.

[21] Appl. No.: 408,927

[22] Filed: Mar. 20, 1995

[51] Int. Cl.$^6$ .................................................. G01N 21/00
[52] U.S. Cl. .......................... 356/338; 356/342; 356/442
[58] Field of Search .............................. 356/338, 342, 356/343, 440, 442; 250/339.113, 573, 574

[56] References Cited

U.S. PATENT DOCUMENTS

| | | |
|---|---|---|
| 2,141,977 | 12/1938 | Gray . |
| 2,714,868 | 8/1955 | Franck . |
| 3,141,094 | 7/1964 | Strickler .................... 250/218 |
| 3,323,484 | 6/1967 | Minkin . |
| 4,064,826 | 12/1977 | Pauli . |
| 4,098,119 | 7/1978 | Coats . |
| 4,184,359 | 1/1980 | Gracey . |
| 4,329,869 | 5/1982 | Toda . |
| 4,524,618 | 6/1985 | Mullis . |
| 4,534,651 | 8/1985 | Minikane ..................... 356/440 |
| 4,945,948 | 8/1990 | Fischer . |
| 5,044,755 | 9/1991 | Landa et al. .................. 356/440 |

Primary Examiner—Frank Gonzalez
Assistant Examiner—Reginald A. Ratliff
Attorney, Agent, or Firm—Freilich Hornbaker Rosen

[57] ABSTRACT

A method and apparatus are provided that indicate the amount of gas such as air in a clear liquid such as water. The apparatus includes a transparent pipe (60), an input coupling (16) at a first end of the transparent pipe, and a shutoff valve (20) at the second end of the pipe. The first end of the pipe is connected to a source of water (12) under pressure, whose air content is to be determined. With the valve (20) open, water is allowed to pass through the pipe and valve to purge the pipe of air and any previous water. The shutoff valve is then closed, to contain the water under pressure. The dissolved air in the static, pressurized water, immediately forms microscopic air bubbles, which result in the water having a "milky" appearance. The presence of the milky appearance indicates the presence of a considerable amount of dissolved water (when the water is not under high pressure). The reflectivity of the water indicates the amount of dissolved air per unit volume of water (when not under high pressure).

8 Claims, 1 Drawing Sheet

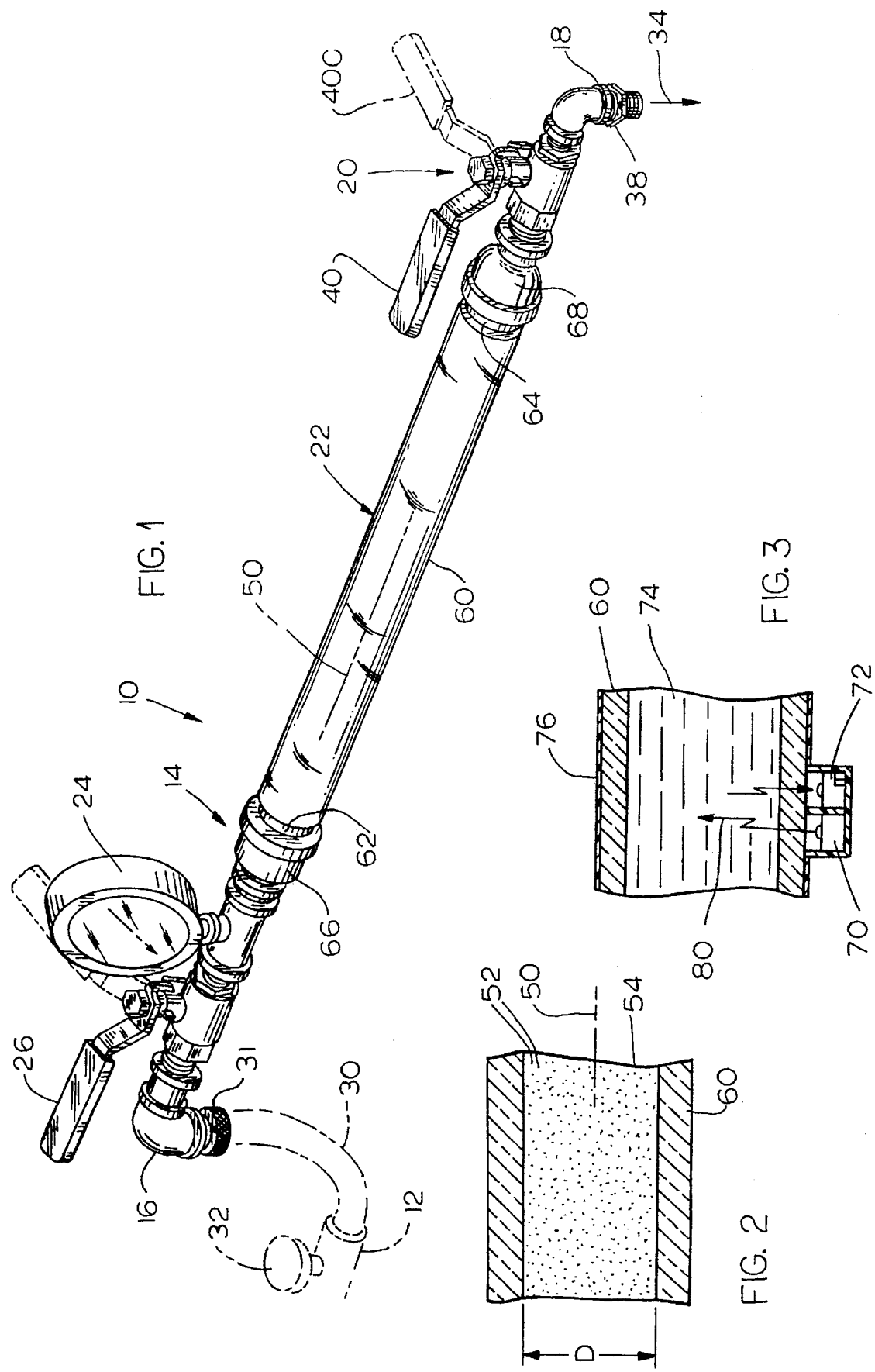

5,636,019

1

AIR-IN-WATER INDICATOR

BACKGROUND OF THE INVENTION

Water obtained from underground wells and other sources, or when air enters a city water supply, often contain large amounts of dissolved air. While there are many tests that can be performed to determine the amount of dissolved air, as by measuring the reaction of the oxygen in the dissolved air, these tests are cumbersome. Air dissolved in water can have many effects, such as producing uneven water "spitting" or spraying and noise when the water pressure is reduced, as when the water exits to the atmosphere. A simple apparatus and method for indicating the presence of significant amounts of dissolved air and/or indicating the amount of dissolved air in water, would be of value.

SUMMARY OF THE INVENTION

In accordance with one embodiment of the present invention, a simple method and apparatus are provided for indicating and/or measuring the presence and/or amount of gas in a clear liquid, such as air in water. The apparatus includes a conduit with first and second ends. A shutoff valve lies at the second end while a portion of the conduit lying between the ends is substantially transparent. With the valve open, water from a pressured supply of the water to be tested, is allowed to flow through the apparatus, to purge the apparatus of air and any previous water therein. With water filling the apparatus, the shutoff valve is closed. This traps pressured water in the apparatus. As soon as the water stops flowing but is contained under a high pressure that is a plurality of times that of atmospheric pressure, microscopic bubbles of air form in the water. By observing the water through the transparent portion of the conduit and noting the pressure of the contained water, a person can note the apparent "milkiness" of the water caused by the myriad microscopic bubbles, which indicates the presence of significant amounts of air in the water. The optical properties of the water, and the pressure at which the milkiness occurs, can indicate the amount of air per unit volume of the water.

The novel features of the invention are set forth with particularity in the appended claims. The invention will be best understood from the following description when read in conjunction with the accompanying drawings.

BRIEF DESCRIPTION OF THE DRAWINGS

FIG. 1 is an isometric view of air indicating apparatus constructed in accordance with one embodiment of the invention, and showing, in phantom lines, the connection of one end of the apparatus to a pressured water tap.

FIG. 2 is a sectional view of the apparatus of FIG. 1, with water lying static therein and indicating microscopic bubbles in the water.

FIG. 3 is a partial sectional view of apparatus constructed in accordance with another embodiment of the invention.

DESCRIPTION OF THE PREFERRED EMBODIMENTS

FIG. 1 illustrates an apparatus 10 that indicates whether or not pressured water from a tap 12 contains a considerable quantity of dissolved air. The particular tap 12 is connected to an underground water source that produces water under a pressure that is usually a plurality of times atmospheric pressure (atmospheric pressure is 15 psi). The presence of a significant amount of dissolved air in the water, may have

2 many effects, as where the oxygen in the water produces a chemical effect (e.g., corrosion of iron pipes and reactions in industrial processes), as well as creating "spitting" and noise when the pressure is reduced to atmospheric. The apparatus 10 includes a conduit 14 having first and second ends 16, 18 with fittings thereat, and with a shutoff valve 20 at the second end. A portion 22 of the conduit is transparent. The apparatus also includes a pressure gauge 24 that indicates the pressure of water within the transparent conduit portion 22, and an additional shutoff valve or valve device 26.

To provide an indication of the presence of substantial quantities of air dissolved in water emanating from the tap 12, the first end 16 of the apparatus is connected to the tap, as by a flexible pipe 30 that connects to a union 31. Initially, both valves 20, 26 are placed in their full open positions. A valve 32 at the tap 12, is opened to allow water from the tap to flow through the flexible pipe 30 and through the apparatus, with the water exiting through the second end 18 of the apparatus as indicated at 34, to flow into a sewer system or onto the ground, or through a "solid" fitting 38 to other pipes. After several seconds of water flow, air and any previous water in the apparatus 10 will have been flushed out. The shutoff valve 20 then is fully closed as by moving a valve handle 40 to the closed position 40C. The pressure of water in the apparatus 10 will rise to the static pressure of water at the tap 12, which will usually be a plurality of times that of atmospheric pressure (i.e. at least about twice atmospheric pressure), and which can be measured by the pressure gauge 24.

Applicant finds that, as soon as the valve 20 is closed, so that high pressure water remains, but is static, that the once-clear water turns "milky". That is, while the water was previously transparent so that almost all light passed through the transparent portion 22 of the apparatus and through the water therein, that the water now transmits significantly less than all of the incident light and reflects a considerable portion of it. This milky or cloudy condition is due to the creation of myriad microscopic bubbles, as a result of the water becoming static at a high pressure of a plurality of atmospheres. It appears that at higher pressures, the water will hold less air in a dissolved state therein. The suddenly air-saturated water produces the microscopic bubbles, which are microscopic in that their average size is no more than 0.01 inch. The pressure at which the air bubbles form, indicates the proportion of air in the water (e.g., cubic centimeters of air at 15 psi per liter of water, both at 72° F.). Thus, the reading of the gauge 24 is useful. It is possible to gradually change the pressure of the water. This can be done, for example, by gradually closing the outlet valve 20, which causes a gradual increase in the pressure of the water and noting the onset and change in the milkiness or cloudiness of the water in the transparent portion 22. It is also possible to initially close the valve 20 and then gradually close the inlet valve 26. As the valve 26 becomes fully closed the pressure of water in the transparent portion 22 of the apparatus falls, which affects the cloudiness of the water, with the fallen pressure being monitorable by the pressure gauge 24.

It is desirable that the transparent part 22 be transparent substantially 360° about its axis 50, that the transparent part be elongated along its axis 50, and that the transparent part have a large inside diameter D (FIG. 2). All of this enables a person to easily observe the degree of cloudiness using ambient light, especially outdoors during the day. While transparent materials such as glass and quartz theoretically could be used, they are easily broken. Transparent plastics are available, but their strength is much less than that of common metals such as brass that are commonly used for pipes, and care must be taken to assure that the transparent pipe portion at 22 will have sufficiently thick walls to withstand the highest pressure that may be encountered, such as 500 psi.

Applicant has constructed and tested a device of the construction shown in FIG. 1. All of the fittings were formed of brass, except for the transparent portion 22 which was formed of a thick walled tube 60 of polycarbonate plastic having a wall thickness of one-quarter inch. The opposite ends 62, 64 of the transparent tube were threaded to produce water tight couplings with brass fittings 66, 68. FIG. 2 illustrates the pipe, with microscopic bubbles 52 in the water 54. The pipe has an inside diameter D of one inch, as compared to the inside diameters of the rest of the fittings such as at the ends 16, 18, which have inside diameters of nominally one-half inch.

FIG. 3 illustrates another embodiment of the invention, where the pipe 60 is used, but a light emitter 70 and light detector 72 are directed at the inside of the pipe, which contains water 74. The outside of the pipe is covered by an opaque black layer 76, to avoid ambient light, and to absorb any light from the emitter 70. When there are no bubbles in the water 74, only a small portion of the emitted light indicated by arrow 80 will be reflected to the detector 72. When the water becomes milky, a higher proportion of the emitted light will be reflected by the water and be detected by the detector 72.

Thus, the invention provides an apparatus and method for indicating the presence of substantial amounts of dissolved air in water, and for measuring it. This is accomplished by an apparatus that includes a transparent conduit portion and a valve that can initially allow the flowthrough of water to expel air, and then stop the flow of water while containing water under a pressure of a plurality of atmospheres. Air initially dissolved in the static pressured water forms myriad microscopic air bubbles, which cause the water to become milky or cloudy. The partial opacity and reflectivity of the milky or cloudy water can be readily observed. The degree of opacity and reflectivity at a particular pressure, and the pressure at which the microscopic bubbles and the cloudiness begin, indicate the amount of dissolved air per unit volume of water.

Although particular embodiments of the invention have been described and illustrated herein, it is recognized that modifications and variations may readily occur to those skilled in the art, and consequently, it is intended that the claims be interpreted to cover such modifications and equivalents.

I claim:

1. A method for measuring the amount of gas dissolved in a substantially clear liquid, comprising:

flowing said liquid into a pipe and then maintaining said liquid at a pressure of a plurality of atmospheres and in a substantially static state in said pipe;

measuring the cloudiness of said liquid while it remains under said pressure and in a substantially static state in said pipe, by directing a beam of energy at said liquid and detecting scattering of said beam of energy.

2. The method described in claim 1 wherein:

said step of measuring cloudiness comprises providing said pipe with a transparent portion, directing light through said transparent portion into said liquid, and observing light reflected from said liquid back through said transparent portion.

3. A method for indicating the amount of air in water, comprising:

flowing said water into a conduit;

maintaining said water substantially static and at a pressure of a plurality of pounds per square inch above atmospheric pressure, in said conduit;

determining the cloudiness of said water while it remains substantially static and under said pressure, by measuring the scattering of light by microscopic bubbles in said water.

4. The method described in claim 3 wherein:

said step of flowing said water, maintaining it under pressure, and determining the cloudiness, includes opening a first valve connected in series with a transparent pipe connecting an end of said transparent pipe opposite said valve to a pressure source of said water and allowing water to flow from said source through said transparent pipe and said valve, closing said valve, and observing the cloudiness of said water through said transparent pipe.

5. Apparatus for indicating the amount of a gas dissolved in a substantially clear liquid, comprising:

a conduit having first and second ends, a fitting at said first end for connection to a pressured water supply, and a valve at said second end;

a portion of said conduit lying between said ends, is substantially transparent, so the degree of cloudiness of pressured liquid therein can be determined by the effect of the liquid on light directed through said transparent portion of said conduit.

6. The apparatus described in claim 5 wherein:

said substantially transparent portion of said conduit is elongated and cylindrical, so ambient light can pass completely through the conduit and fully illuminate a length of the liquid.

7. The apparatus described in claim 6 including:

a second valve device lying between said transparent conduit portion and said first end of said conduit, said second valve device being gradually closeable to enable a controlled decrease in water pressure in said transparent portion of said conduit.

8. The apparatus described in claim 5 including:

a light emitter positioned to direct light at water in said transparent portion of said conduit, and a light detector positioned to detect light reflected from said liquid that is illuminated by said light emitter.

* * * * *